(12) United States Patent
Kumazawa et al.

(10) Patent No.: US 7,677,081 B2
(45) Date of Patent: Mar. 16, 2010

(54) METHOD FOR ANALYZING GAS COMPONENTS, APPARATUS FOR SEPARATING GAS COMPONENTS AND METHOD FOR IDENTIFYING THE SAME

(75) Inventors: Hidehiro Kumazawa, Toyama (JP); Ken-Ichi Sakurai, Nagaoka (JP); Yoshitaka Ikarashi, Nagaoka (JP)

(73) Assignee: Kabushiki Kaisha Onsui, Niigata (JP)

( * ) Notice: Subject to any disclaimer, the term of this patent is extended or adjusted under 35 U.S.C. 154(b) by 301 days.

(21) Appl. No.: 11/806,347

(22) Filed: May 31, 2007

(65) Prior Publication Data
US 2008/0276686 A1    Nov. 13, 2008

(30) Foreign Application Priority Data
Oct. 11, 2006    (JP)    ............... 2006-277660

(51) Int. Cl.
*G01N 1/28* (2006.01)
*G01N 33/50* (2006.01)
(52) U.S. Cl. .................................... 73/23.41
(58) Field of Classification Search .......... 73/23.41, 73/23.35, 23.2; 366/140, 273, 279
See application file for complete search history.

(56) References Cited
U.S. PATENT DOCUMENTS
4,892,832 A * 1/1990 Omote et al. ............ 435/297.1

6,842,009 B2 * 1/2005 Potter ....................... 324/633
2004/0252582 A1 * 12/2004 Bucher ...................... 366/273
2007/0099189 A1 * 5/2007 Gomez-Elvira Rodriguez et al. ......................... 435/6

FOREIGN PATENT DOCUMENTS

| JP | 11-030612 A | 2/1999 |
| JP | 2002-204650 A | 7/2002 |
| JP | 2002-315599 A | 10/2002 |
| JP | 2004-129627 A | 4/2004 |
| JP | 2004-317260 A | 11/2004 |
| JP | 2007-501405 A | 1/2007 |
| WO | 01/83594 A1 | 11/2001 |

* cited by examiner

*Primary Examiner*—Lisa M Caputo
*Assistant Examiner*—Punam Patel
(74) *Attorney, Agent, or Firm*—Sughrue Mion, PLLC

(57) ABSTRACT

The present invention provides a method for analyzing gas components, an apparatus for separating the gas components, and a method for identifying the gas components that can provide more accurate information in distribution and consumption by classifying and identifying products that have been subjected to carbon monoxide treatment. The present invention provides a method for quantitatively analyzing gas components contained in a specimen, wherein an untreated specimen having an unchanged solid state and a prescribed weight is placed in an airtight container in which a solution is accommodated; the specimen is homogenized in the airtight container; and the gas components contained the specimen are quantitatively analyzed.

13 Claims, 7 Drawing Sheets

METHOD FOR ANALYZING GAS COMPONENTS, APPARATUS FOR SEPARATING GAS COMPONENTS AND METHOD FOR IDENTIFYING THE SAME

BACKGROUND OF THE INVENTION

1. Field of the Invention

The present invention relates to a method for analyzing gas components, an apparatus for separating gas components, and a method for identifying the same.

2. Description of the Related Art

Currently, subjecting harvested fish to carbon monoxide treatment (CO treatment) using the method disclosed in, e.g., Patent Document 1, or using other methods is prohibited in Japan. Fresh fish imported from foreign countries is quantitatively analyzed by public inspection agencies using a method for analyzing carbon monoxide (hereinafter referred to as "method A") contained in fresh fish, and a determination is made whether the fresh fish have been subjected to carbon monoxide treatment.

Specifically, method A is a method for quantitatively analyzing carbon monoxide containing fish, which entails adding twice the amount of water to 300 g of fish cut in thin slices; homogenizing the system for 1 minute under ice water using a homogenizer to obtain a sample fluid; placing 200 g of the sample fluid in a centrifuge and centrifuging the sample fluid at 10° C.; using the supernatant as the sample solution and subsequently placing 50 mL of the sample solution in a headspace bottle; adding 20 mL of 20% sulfuric acid, 5 mL of water, and 5 drops of octyl alcohol as an antifoaming agent; placing a cover having a silicone rubber stopper on the headspace bottle and vigorously shaking the bottle for 2 minutes; leaving the solution stationary for 10 minutes and then shaking the solution again for 1 minute; and immediately collecting the gas phase in the bottle into a gastight syringe and injecting the gas phase into a gas chromatograph to calculate the carbon monoxide concentration in the sample by using a separately prepared calibration curve.

When the quantitative value is 200 μg/kg or higher on the first day of testing, and the quantitative value two days later is clearly less than the quantitative value of the first day of testing, or when the quantitative value of the first day of testing is 500 (g/kg or higher, tuna or other types of fresh fish are determined to have been subjected to carbon monoxide treatment.

Professor Hidehiro Kumazawa and others of University of Toyama produced a plurality of uniform specimens from the same samples in order to ascertain the validity of method A, requested that the following three public inspection agencies perform an analysis of carbon monoxide in fish, and obtained the measurement results shown in TABLE 1.

TABLE 1

|  | Carbon monoxide concentration/(μg/kg) | | |
|---|---|---|---|
| Inspection Agency | Specimen A | Specimen B | Specimen C |
| Inspection Agency A | 75/120 | 1,100/980 | 1,000/940 |
| Inspection Agency B | 270/280 | 350/420 | 600/540 |
| Inspection Agency C | 640/470 | 571/607 | 352/364 |

There is a considerable measurement error, i.e., about 140%, from a minimum of 75 (g/kg and a maximum of 1,100 (g/kg, as shown in Table 1, and it is apparent from the experiment performed by Professor Hidehiro Kumazawa and others that method A has a reproducibility problem.

At least the following three problems can be given as causes of the measurement error.

1) Measurement Errors in the Homogenizing Stage

When a specimen is homogenized in ice water for 1 minute, it is presumed that all of the carbon monoxide is sealed within the sample solution, but this does not mean that homogenization occurs in the airtight space in particular. It is unavoidable that carbon monoxide present in the myoglobin (hereinafter referred to as "Mb") of the fish is diffused throughout the gas.

2) Errors in the Centrifuging Stage

The fluid is centrifuged and the supernatant is used as the sample solution, but all of the carbon monoxide must be transferred to the supernatant at this time. However, since the solubility of carbon monoxide in an aqueous solution is very low, it is doubtful that all of the carbon monoxide has been dissolved in the supernatant. The undissolved carbon monoxide dissipates in the gas.

3) Errors in the Fabrication Stage of the Injection Gas Sample for Gas Chromatography It is presumed that all of the carbon monoxide is transferred to the gas phase after a prescribed amount of the sample solution or other fluid is placed in a headspace bottle and the bottle is shaken and left standing, but a carbon monoxide concentration that is in balance with at least the carbon monoxide concentration in the gas phase remains in the liquid phase.

In view of the above, Professor Kumazawa solved the problem of method A by analyzing the gas components contained in the fish in the airtight circuit, and developed the highly reproducible Kumazawa Method (hereinafter referred to as the "KH method"). TABLE 2 shows the results of an analysis using the same samples as those shown in TABLE 1.

TABLE 2

|  | Carbon monoxide concentration/(μg/kg) | | |
|---|---|---|---|
| Inspection Agency | Specimen A | Specimen B | Specimen C |
| KH Method (Kumazawa Method) | D 1,490/1,310<br>G 1,430/1,180 | 1,480/1,240<br>1,470/1,220 | 1,220/1,040<br>1,200/1,050 |

*D: CO concentration measurement using a detector tube
*G: CO concentration measurement using gas chromatography The KH method for analyzing the carbon monoxide contained in fish is described in detail below.

The measuring apparatus of the KH method is shown in FIG. 1. A prescribed amount of fish is weighed, cut into 5 mm pieces, and used as samples. The samples are placed in boiling water 32 in flasks 31, and the gas components desorbed and diffused from the samples are collected into Tedlar bags 36 together with nitrogen gas injected from an injection port 35 connected by way of a pressure regulating value 33 and a flow meter 34. The water vapor emitted from the boiling water is condensed in a condenser 37 and returned to the flask. The gas components recovered in the Tedlar bags 36 are quantified using gas chromatography and gas sensors or detection tubes.

However, the KH method has the following problems.

In order to confirm that the gas components contained in the fish are diffused into the atmosphere, smoke treated tuna having a known surface area was placed into a container and the container was with 1 L of nitrogen, and the change in the carbon monoxide concentration in the container over time was measured. The results are shown in FIG. 2. The gas components can be confirmed to have diffused into the gas phase, which is the case of the measurement principle of method B as an officially authorized measurement method.

Also, the amount diffused can be confirmed to be proportional to the surface area of the fish. It is therefore concluded that the gas components are diffused into the atmosphere when the samples are being prepared. When the gas components are recovered from the samples in the KH method, the components are recovered together with the nitrogen gas. Therefore, the gas components are diluted by the nitrogen gas, and it becomes difficult to quantify low-content gas components. Also, since the samples are 5 mm pieces, the method is laborious because a considerable amount of time is required to separate the gas components in the center of the samples.

[Patent Document 1] Japanese Laid-open Patent Application No. 2004-129627.

SUMMARY OF THE INVENTION

An object of the present invention is to provide a method for analyzing gas components, an apparatus for separating the gas components, and a method for identifying the gas components, wherein the problems in the KH method described above are improved, the gas components contained in fish or meat, for example, can be rapidly separated, high sensitivity and excellent reproducibility are provided, and more accurate information in distribution and consumption can be obtained by classifying and identifying products subjected to carbon monoxide treatment in the marketplace in which smoked or synthetic carbon monoxide is diluted or left unchanged and brought into contact and absorbed into fish or meats or an assortment of untreated manufactured products.

The main points of the present invention will be described with reference to the attached drawings.

There is provided a method for quantitatively analyzing gas components contained in a specimen, the method comprising placing an untreated specimen having an unchanged solid state and a prescribed weight in an airtight container in which a solution is accommodated; homogenizing the specimen in the airtight container; and quantitatively analyzing the gas components contained in the specimen.

In the method for analyzing gas components according to the first aspect, the specimen is homogenized in a state in which a saturated aqueous solution is placed as the solution in the airtight container, or the interior of the airtight container is heated or decompressed.

In the method for analyzing gas components according to the second aspect, the gas components contained in the specimen are quantitatively measured so that fish or meat as the specimen can be identified to be carbon monoxide treated, smoked, or untreated.

In the method for analyzing gas components according to the third aspect, the identification is carried out by quantitatively analyzing the gas components, e.g., carbon monoxide and lower hydrocarbon groups contained in the specimen.

In the method for analyzing gas components according to the third aspect, the specimen is homogenized in a state in which an aqueous solution having a pH of 2.77 or less is placed as the solution in the airtight container.

In the method for analyzing gas components according to the fourth aspect, the specimen is homogenized in a state in which an aqueous solution having a pH of 2.77 or less is placed as the solution in the airtight container.

In the method for analyzing gas components according to any of the first to sixth aspects, the specimen is homogenized and the gas phase volume inside the airtight container is thereafter temperature or pressure corrected.

In the method for analyzing gas components according to any of the first to sixth aspects, the specimen is homogenized, and the saturated aqueous solution is thereafter injected into the airtight container to extract the gas inside the airtight container.

In the method for analyzing gas components according to the seventh aspect, the specimen is homogenized, and the saturated aqueous solution is thereafter injected into the airtight container to extract the gas inside the airtight container.

In the method for analyzing gas components according to the ninth aspect, the specimen is homogenized, and the gas components separated inside the airtight container are quantified using gas chromatography and gas sensors or detection tubes.

There is provided an apparatus for separating gas components in which gas components contained in a specimen are separated using the method for analyzing gas components according to any of the first to sixth aspects, the apparatus comprising an airtight container capable of accommodating the specimen, and a homogenizer capable of homogenizing the specimen in the airtight container while maintaining an airtight state.

There is provided an apparatus for separating gas components in which gas components contained in a specimen are separated using the method for analyzing gas components according to the seventh aspect, the apparatus comprising an airtight container capable of accommodating the specimen, and a homogenizer capable of homogenizing the specimen in the airtight container while maintaining an airtight state.

There is provided an apparatus for separating gas components in which gas components contained in a specimen are separated using the method for analyzing gas components according to the eighth aspect, the apparatus comprising an airtight container capable of accommodating the specimen, and a homogenizer capable of homogenizing the specimen in the airtight container while maintaining an airtight state.

There is provided an apparatus for separating gas components in which gas components contained in a specimen are separated using the method for analyzing gas components according to the ninth aspect, the apparatus comprising an airtight container capable of accommodating the specimen, and a homogenizer capable of homogenizing the specimen in the airtight container while maintaining an airtight state.

There is provided an apparatus for separating gas components in which gas components contained in a specimen are separated using the method for analyzing gas components according to the tenth aspect, the apparatus comprising an airtight container capable of accommodating the specimen, and a homogenizer capable of homogenizing the specimen in the airtight container while maintaining an airtight state.

There is provided a method for quantitatively analyzing gas components, e.g., carbon monoxide and lower hydrocarbon groups contained in fish, meat, or another specimen, and identifying the specimen to be CO treated, smoked, or untreated, the method comprising placing a saturated aqueous solution having a pH of 2.77 or less in an airtight container; mixing a liquid phase and gas phase in the airtight container and simultaneously substituting an inert atmosphere in place of the gas phase, and thereafter placing an untreated specimen having an unchanged solid state and a prescribed weight in the airtight container in which an inert gas has been substituted in place of the gas phase; releasing the gas components, e.g., carbon monoxide and lower hydrocarbon groups contained in the specimen into the gas phase by homogenizing the specimen, the liquid phase, and the gas phase in the airtight container; and quantitatively analyzing the carbon monoxide and lower hydrocarbon groups released into the gas phase.

There is provided a method for quantitatively analyzing gas components, e.g., carbon monoxide and lower hydrocarbon groups contained in fish, meat, or another specimen, and identifying the specimen to be CO treated, smoked, or untreated, the method comprising placing an aqueous solution having a pH of 2.77 or less in an airtight container; mixing a liquid phase and gas phase in the airtight container and simultaneously substituting an inert atmosphere in place of the gas phase, and thereafter placing an untreated specimen having an unchanged solid state and a prescribed weight in the airtight container in which an inert gas has been substituted in place of the gas phase; releasing the gas components, e.g., carbon monoxide and lower hydrocarbon groups contained in the specimen into the gas phase by substituting an inert gas in place of the gas phase in the airtight container, and homogenizing the specimen, the liquid phase, and the gas phase in the airtight container in a state in which the airtight container has been heated or decompressed; and quantitatively analyzing the carbon monoxide and lower hydrocarbon groups released into the gas phase.

In view of the foregoing, the present invention provides a method for analyzing gas components, an apparatus for separating the gas components, and a method for identifying the gas components, wherein the gas components contained in fish or meat, for example, can be rapidly separated, high sensitivity and excellent reproducibility can be provided, and more accurate information in distribution and consumption can be obtained by classifying and identifying products subjected to carbon monoxide treatment in the marketplace in which smoked or synthetic carbon monoxide is diluted or left unchanged and brought into contact and absorbed into fish or meats or an assortment of untreated manufactured products.

DESCRIPTION OF THE PREFERRED EMBODIMENTS

Figure 1:
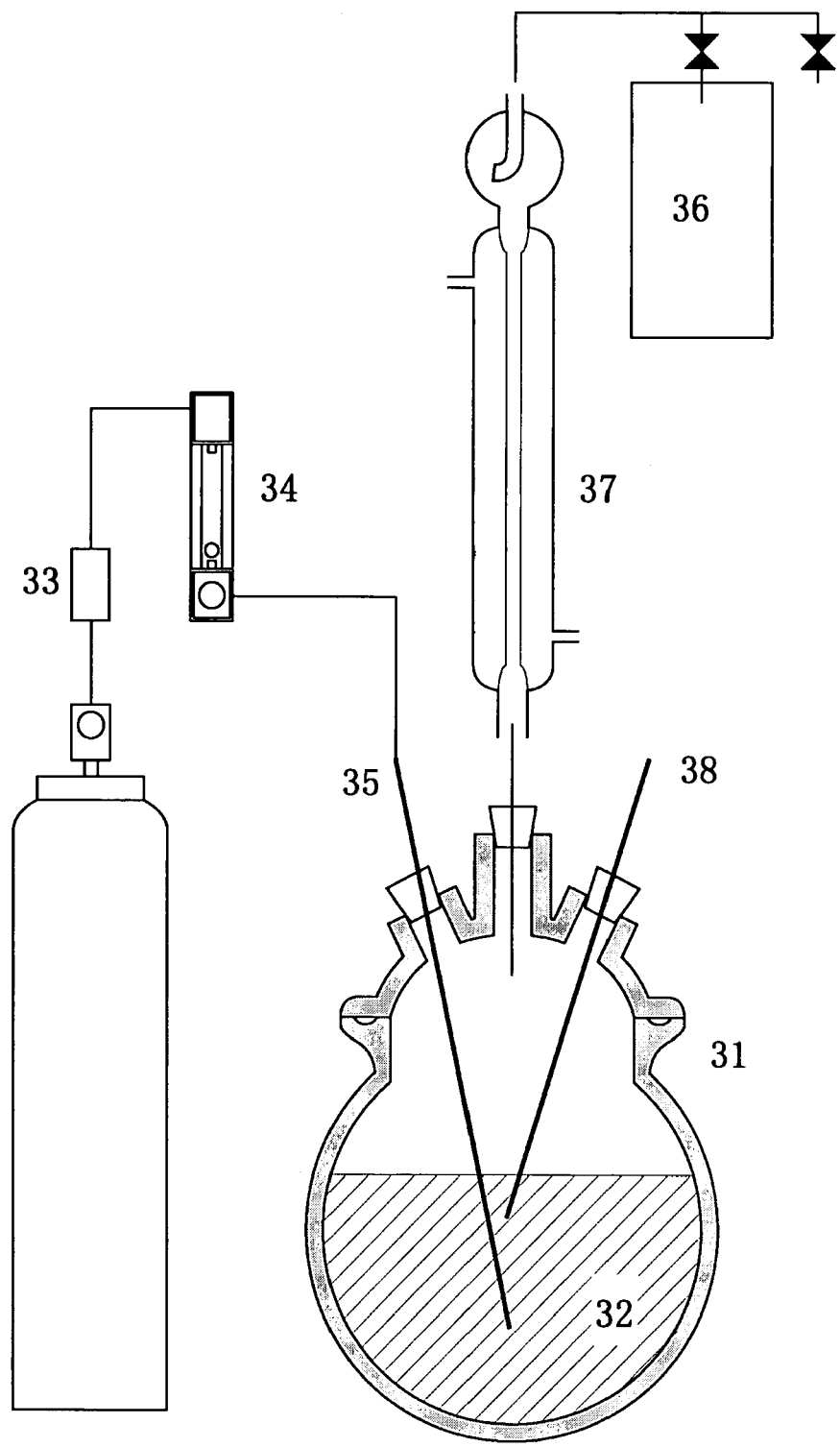
FIG. 1 is a schematic explanatory diagram of a conventional example.
Figure 2:
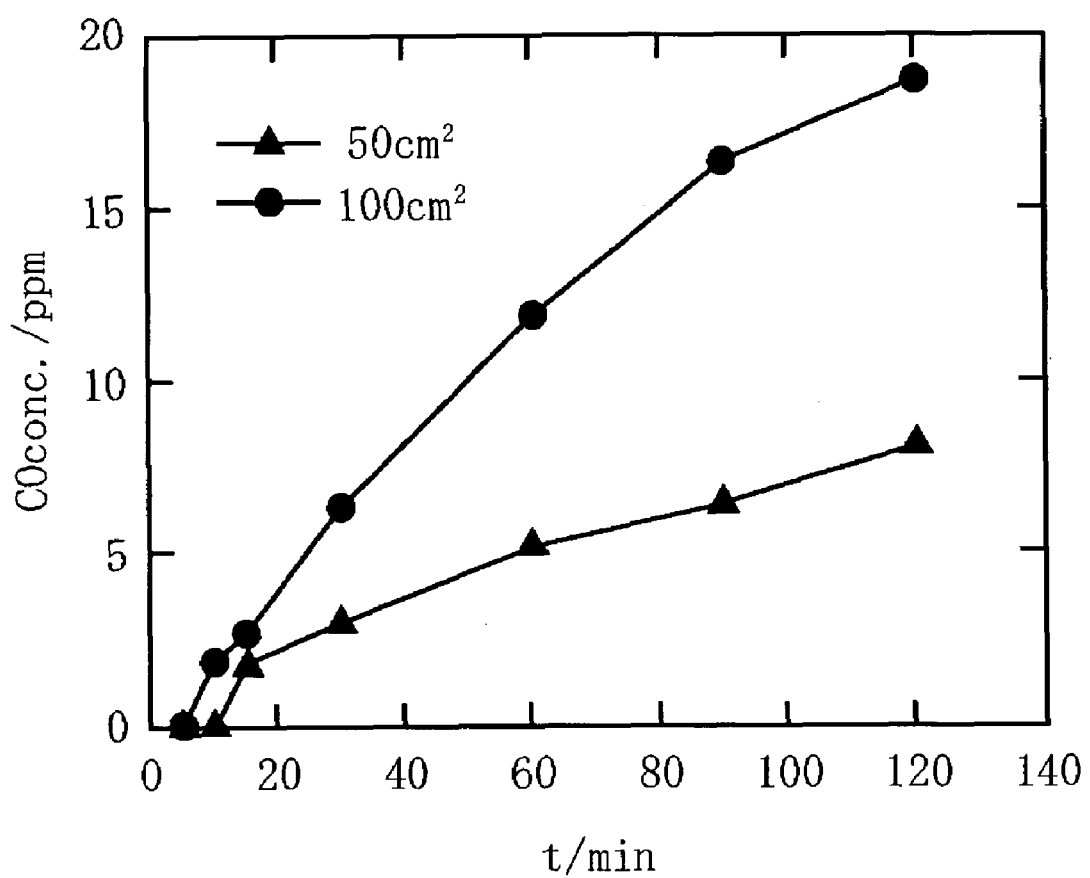
FIG. 2 is a graph showing the observation results of the change over time in a carbon monoxide concentration in a container.

Embodiments (how the present invention is implemented) of the present invention considered to be advantageous are briefly described and the effects of the present invention are described with reference to the drawings.

A specimen having a prescribed weight is homogenized in an airtight container, whereby the carbon monoxide, lower hydrocarbon groups, and other gas components contained in the specimen are kept inside the airtight container and do not dissipate when transferred to the gas phase.

Specifically, the specimen having a minimized surface area is placed in an airtight container without being homogenized, shredded, or otherwise pretreated, and is thereafter homogenized inside the airtight container, whereby the dissipation of the gas components to the exterior of the airtight container can be minimized, and errors due to the dissipation of gas components from the specimen prior to placement in the airtight container can be reduced.

The gas components contained in the specimen can therefore be more accurately analyzed, and the carbon monoxide and lower hydrocarbon groups are quantitatively analyzed to allow fish and meat as the specimen to be more accurately identified as having been subjected to CO treatment or smoking treatment, or as having not been so treated.

For example, the gas components can be prevented from remaining in the liquid phase during homogenization by bringing salts in the solution inside the airtight container to saturation in order to facilitate the movement of gas components from the liquid phase to the gas phase, by heating or decompressing the interior of the airtight container, or by otherwise reducing the solubility of the gases.

In other words, by reducing the solubility of the gases, an environment can be formed that facilitates the movement of the gas components to the gas phase, and errors due to gas components remaining in the liquid phase can be reduced.

Also, the pH of the aqueous solution inside the airtight container is set to, e.g., 2.77 or less, whereby the gas components in the hemoglobin (hereinafter referred to as "Hb") and Mb are more easily dissociated, the movement of the gas components physically dissolved in the meat to the gas phase is facilitated, and errors due to the gas components in the Hb and Mb not becoming dissociated can be reduced.

Therefore, the present invention solves the problems of the KH method, is able to detect the gas components contained in a specimen with higher accuracy and good reproducibility, and can quantitatively analyze, e.g., carbon monoxide, lower hydrocarbon groups, and other gas components contained, e.g., in fish and meats to more reliably identify whether fish and meats have been CO treated, are smoked products, or are untreated products.

Embodiments

Specific embodiments of the present invention will be described with reference to the diagrams.

The present embodiment is a method for quantitatively analyzing gas components, e.g., carbon monoxide and lower hydrocarbon groups contained in fish, meats, and other specimens, and identifying whether a specimen has been CO treated, is a smoked product, or is an untreated product. The method comprises placing a saturated aqueous solution having a pH of 2.77 or less in an airtight container; mixing a liquid phase and gas phase in the airtight container and simultaneously substituting an inert atmosphere in place of the gas phase; placing an untreated specimen having an unchanged solid state and a prescribed weight in the airtight container in which an inert gas has been substituted in place of the gas phase; releasing the gas components, e.g., carbon monoxide and lower hydrocarbon groups contained in the specimen into the gas phase by homogenizing the specimen, the liquid phase, and the gas phase in the airtight container; and quantitatively analyzing the carbon monoxide and lower hydrocarbon groups released into the gas phase.

Each step will be described in detail.

The present embodiment is a method for homogenizing the specimen in a state in which a salt-saturated aqueous solution is placed as the above-mentioned solution in the airtight container. The saturated solution of the present invention is not limited to salts. Other saturated aqueous solutions may be used, and the airtight container may be heated or decompressed when homogenization is performed. In essence, the solubility of the gas components with respect to the aqueous solution is minimized, and an environment is formed that facilitates the movement of the gas components contained in the specimen from the liquid phase to the gas phase.

Sulfuric acid is mixed into the solution to bring the pH to 2.77 or less. The pH may be brought to 2.77 or less by mixing other acids, but depending on the type of acid, gases are generated during homogenization, and reproducibility may be compromised. Sulfuric acid is therefore preferably employed.

In the present embodiment, the specimen is homogenized and the volume of the gas phase inside the airtight container is temperature and pressure compensated. The quantitative analysis of the gas components can be performed under uniform conditions, and measurement errors caused by differences in the analysis location can be eliminated.

In the present embodiment, when and after the specimen is homogenized, the gas phase inside the airtight container can be easily removed and recovered into a Tedlar bag. Specifically, the gas phase (separated gas) inside the airtight container is easily removed by injecting a salt-saturated aqueous solution in the container via an injection port.

Therefore, the gas components can be quantified even when a fixed quantity of separated gas is required in the quantification carried out by a detection tube, various gas component sensors, or the like.

After the specimen has been homogenized, the gas components separated in the airtight container are quantified using known gas chromatography, various gas sensors, or various detection tubes.

As used in the present embodiment, homogenization refers to the process of crushing/shredding a specimen using a homogenizer (cutter, mill, or the like) and stirring the homogenized product with a solution to make a uniform system.

The reason for selecting a configuration such as that described above is described in detail below.

The KH method and method A are performed in an open space, but the present embodiment entails placing a specimen having a prescribed weight in a closed circuit (airtight container) to perform homogenization, rather than homogenizing, shredding, or carrying out other work in an open space in the sample formation step.

The present embodiment entails bringing salts in the solution in the container to saturation to reduce the solubility of the gases in order to facilitate the movement of the gas components from the liquid phase to the gas phase during homogenization.

Figure 3:
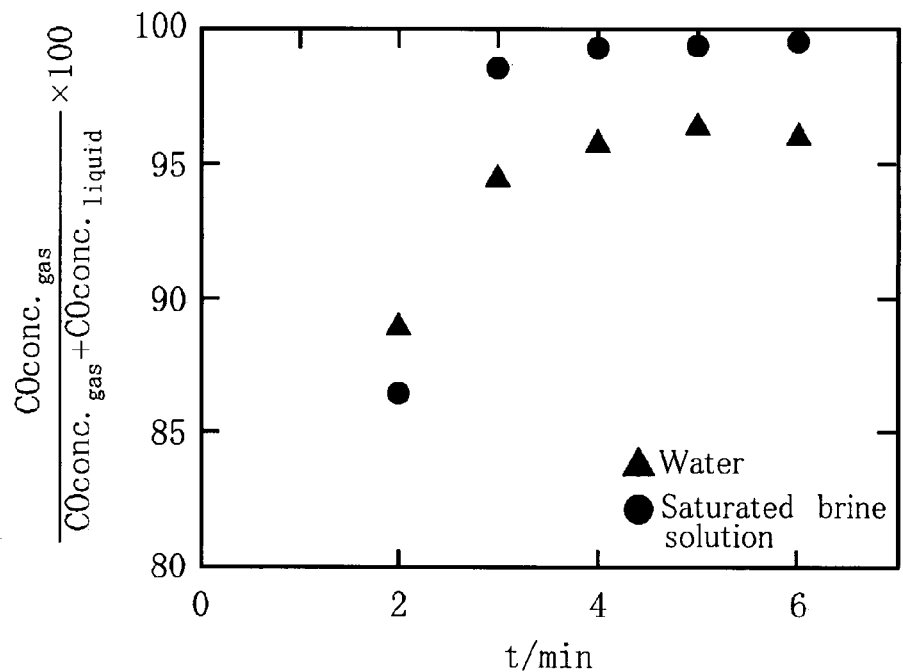
FIG. 3 is a graph showing the observation results of the change in a vapor phase carbon monoxide concentration when a saturated brine solution is placed together with fish in an airtight container and homogenized.

Specifically, the problem of method A in which gas components remain in the liquid phase can also occur in the same manner in the present embodiment. However, this problem is solved by creating an environment that facilitates the movement of the gas components to the gas phase by saturating the solution using salts and reducing the solubility, which can be seen in FIG. 3. The drawing shows the results of observing the change in carbon monoxide concentration of the gas phase when a saturated brine solution is placed together with fish in an airtight container and homogenized. In the present embodiment, a salt (NaCl) whose solubility is weakly dependent on temperature is employed, and consideration is given to solubility changes that occur together with increases in the temperature during measurement.

In the present embodiment, the pH of the aqueous solution inside the closed circuit is set, e.g., to 2.77 or less in order to facilitate the dissociation of gases that are coordination-bonded with the Hb and Mb of fish and meat.

If the color of the meat is a fresh red color, the meat is determined to be good-quality meat, and if the color is brown, the meat is considered to be old and other judgments are made in which the color tone considerably affects a consumer's evaluation and eagerness to purchase the product. The primary coloring matter directly related to color tone is the Hb and Mb present in fish and meats.

Figure 4:
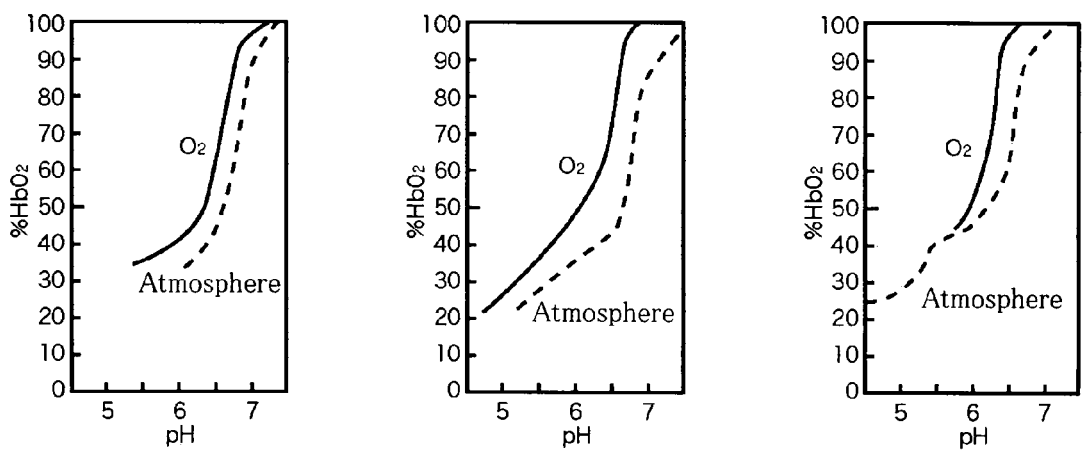
FIG. 4 is a graph showing the relationship between the saturation level (%) and the pH when oxygen and the atmosphere having the same pressure are balanced in three types of blood.

FIG. 4 shows the relationship between the saturation level (%) and the pH when oxygen and the atmosphere having the same pressure are balanced in three types of blood. In relation to Hb in fish and meats, it is apparent that the saturation percentage of oxygen in the Hb of fish and meats gradually decreases as the pH is reduced.

The Mb of fish and meats is considered to have essentially the same reaction mechanism as Hb in relation to color and physical properties, and oxymyoglobin ($O_2$ Mb) facilitates the dissociation of oxygen and promotes autooxidation in association with a lower pH. The amount of metmyoglobin generated after a fixed storage period will increase and the color will change.

In view of the above, in the present embodiment, the pH of the aqueous solution in the closed circuit is brought to 2.77 or less, whereby the gas components in the Hb and Mb are more easily dissociated.

TABLE 3 shows the results of adding twice the amount of water with respect to tuna, homogenizing the system, adding sulfuric acid in small amounts to the resulting solution, and measuring the L, a, and b values of each level of pH.

TABLE 3

| pH | L value | a value | b value |
| --- | --- | --- | --- |
| 6.02 | 50 | 39 | 19 |
| 4.73 | 54 | 20 | 14 |
| 3.60 | 56 | 12 | 15 |
| 2.77 | 56 | 11 | 12 |
| 1.41 | 55 | 11 | 11 |

It is apparent from TABLE 3 that the change in the color tone is reduced as the pH is reduced, and the color tone stops changing at a fixed pH or less. Therefore, it is believed that the gas components in a coordination bond in the Mb and Hb become completely dissociated by bringing the pH of the solution to 2.77 or less. The chemically bonded gas components can also therefore be recovered, which allows the analysis to be commensurately improved.

When homogenization is carried out, an anti-foaming material is added in a suitable amount in order to reduce the generation of foam caused by higher viscosity.

TABLE 4 shows the recovery rate and results of quantifying the lower hydrocarbon groups contained in a smoke-treated product, the lower hydrocarbon groups being CO, methane ($CH_4$), acetylene ($C_2H_2$), ethylene ($C_2H_4$), ethane ($C_2H_6$), propylene ($C_3H_6$), propane ($C_3H_8$), and normal butane (n-$C_4H_{10}$).

TABLE 4

| Specimen No. | Concentration of gas components/(μg/kg) | | | | | | | |
| --- | --- | --- | --- | --- | --- | --- | --- | --- |
|  | CO | $CH_4$ | $C_2H_2$ | $C_2H_4$ | $C_2H_6$ | $C_3H_6$ | $C_3H_8$ | n-$C_4H_{10}$ |
| 1 | 6352 | 1295 | 37 | 2308 | 180 | 356 | 22 | 158 |
| Recovery rate | 98.8 | 100 | 100 | 100 | 100 | 100 | 100 | 100 |

TABLE 4-continued

| Specimen | Concentration of gas components/(μg/kg) | | | | | | | |
|---|---|---|---|---|---|---|---|---|
| No. | CO | $CH_4$ | $C_2H_2$ | $C_2H_4$ | $C_2H_6$ | $C_3H_6$ | $C_3H_8$ | $n\text{-}C_4H_{10}$ |
| 2 | 6337 | 1329 | 39 | 2374 | 165 | 346 | 24 | 146 |
| Recovery rate | 98.9 | 100 | 100 | 100 | 100 | 100 | 100 | 100 |

The analysis of the carbon monoxide in TABLE 4 was performed using a gas chromatograph (GC-14B) having a methanizer (Shimadzu MTN-1). The separation column (SUS I.D 3 m) was filled with molecular sieve 13X, He was used as the carrier gas, hydrogen was used for CO reduction, FID was used for detection, and the concentration was determined.

The analysis of the lower hydrocarbon groups, i.e., $CH_4$, $C_2H_2$, $C_2H_4$, $C_2H_6$, $C_3H_6$, $C_3H_8$, and $n\text{-}C_4H_{10}$ was carried out by separating the components under increasing temperature conditions (40 to 120° C., temperature increase rate: 5° C./min) using a gas chromatography in which Unipak S as the separation column (SUS I.D 3 m) was filled to 2 m, and thereafter performing detection using FID to determine the concentration. He was used as the carrier gas.

It was confirmed from TABLE 4 that the present embodiment can yield better results than conventional measurement methods in terms of reproducibility and the recovery rate of the gas components contained in the specimen, and that the separation of the gas components contained in fish can be completed in a short period of time.

Figure 8:
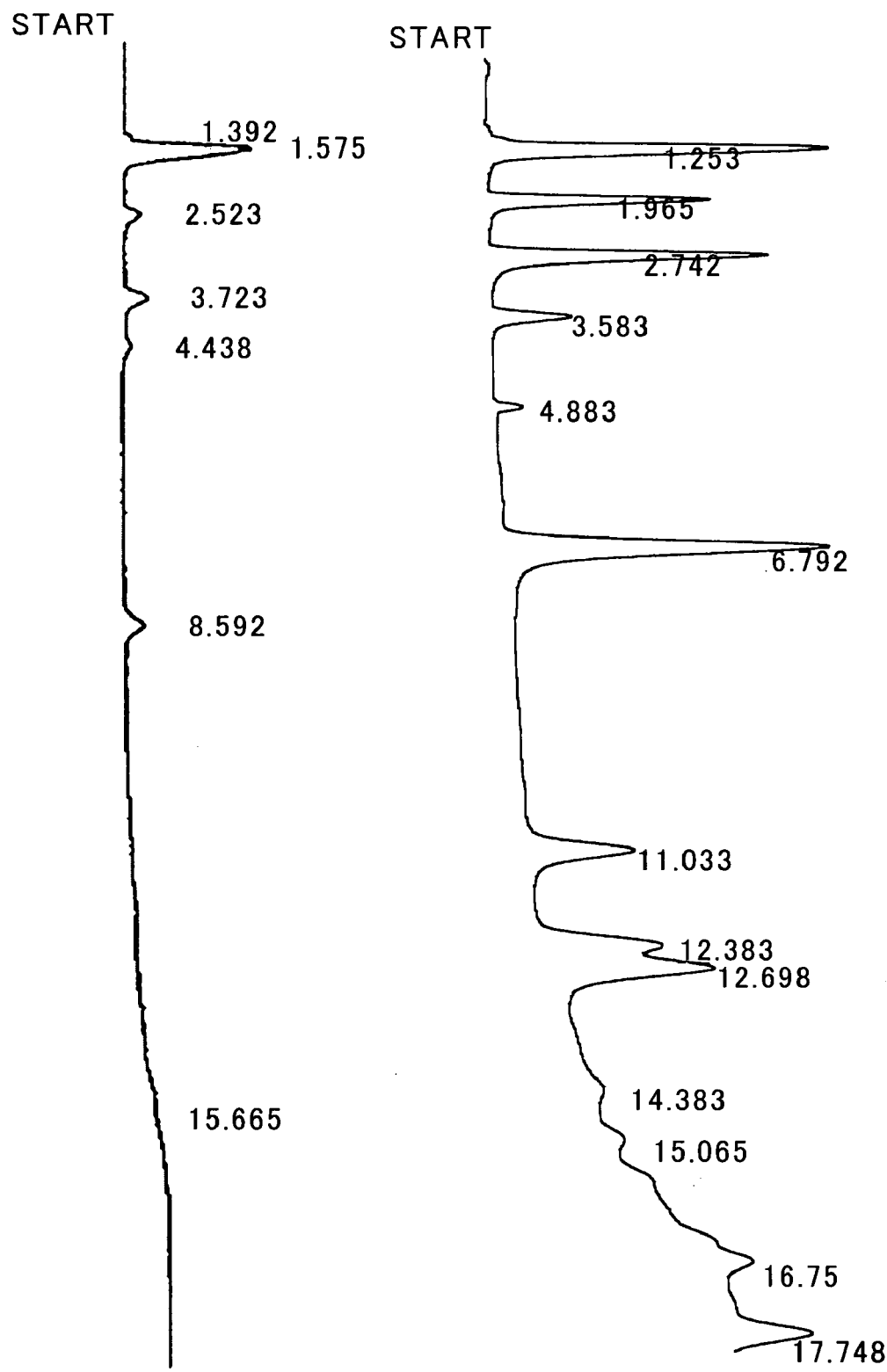
FIG. 8 is a chromatograph of separated gas components.

The concentration of the separated gas is about six times greater than the concentration of gas recovered using the KH method, and $C_2H_2$ and $n\text{-}C_4H_{10}$ can therefore be detected, which is not possible using the KH method. FIG. 8 shows a chromatograph of actual measurements of gas components separated using the Kumazawa method and gas components separated in the present embodiment. The left side is a chromatograph of the Kumazawa method and the right side is a chromatograph of the present embodiment. In the present embodiment, seven types of lower hydrocarbon groups were used as the indices for identifying carbon monoxide treated products and smoked products. When the separation apparatus of the present embodiment was used, the gas components contained in the smoked monoxide and the number of components that could be detected were increased, as shown in FIG. 8. Therefore, the number of identification indices can be increased.

TABLE 5 shows the results of analyzing the gas components contained in untreated products and carbon monoxide treated products.

TABLE 5

| Specimen | Concentration of gas components/((g/kg) | | | | | | | |
|---|---|---|---|---|---|---|---|---|
| No. | CO | $CH_4$ | $C_2H_2$ | $C_2H_4$ | $C_2H_6$ | $C_3H_6$ | $C_3H_8$ | $n\text{-}C_4H_{10}$ |
| Untreated product | 63 | 31 | 0 | 0 | 0 | 0 | 0 | 0 |
|  | 61 | 39 | 0 | 0 | 0 | 0 | 0 | 0 |
| CO-treated product | 7236 | 20 | 0 | 0 | 0 | 0 | 0 | 0 |
|  | 7240 | 21 | 0 | 0 | 0 | 0 | 0 | 0 |

Comparing TABLES 4 and 5, it can be said that an untreated product, a smoked product, and a carbon monoxide product each contain specific gas components. Therefore, the components can be classified and identified by quantitatively analyzing the lower hydrocarbon groups.

A tube for nitrogen gas is fitted to the separation apparatus, and nitrogen is substituted into the separable flask. A raw or frozen specimen is then placed in the apparatus. The effect of interference gas on the gas sensors can be reduced and measurement errors caused by gas components eliminated by again substituting nitrogen gas.

After fish or meat has been homogenized inside the closed system, measurement errors due to measurement environment difference can be eliminated by providing an extraction unit for extracting the gas phase using a gas syringe, and by providing a temperature compensator, a volume compensator, a nitrogen gas tube, and a thermostat.

After homogenization, a salt-saturated aqueous solution is injected from a tube mounted on the lower portion of a separable flask, whereby the gas phase can be collected into a Tedlar bag via a tube provided to the upper portion of the main body, and the concentration of the gas components can be measured using gas sensors and detection tubes.

The detection sensitivity can be determined by the volume of the separable flask and the quantity of solution. When, for example, homogenization is performed using a separable flask having a capacity of 1,000 mL and using 500 mL of a salt-saturated aqueous solution, 500 mL of separated gas is obtained, which corresponds to a detection sensitivity that is about 6 times greater than that of the KH method.

The specific procedures of the present embodiment are described below using a specific example of the separation apparatus.

The samples (specimens) of the present embodiment were obtained by thawing a frozen product and vacuum packing and freezing the product immediately thereafter; by peeling the skin from the fresh product to obtain strips and vacuum packing and freezing the product immediately thereafter; and by peeling the skin from slices and vacuum packing and freezing the slices immediately thereafter. About 30 to 60 g were collected from the frozen strips or the frozen slices. These will be referred as "sample A."

[Analysis Method 1]

Figure 5:
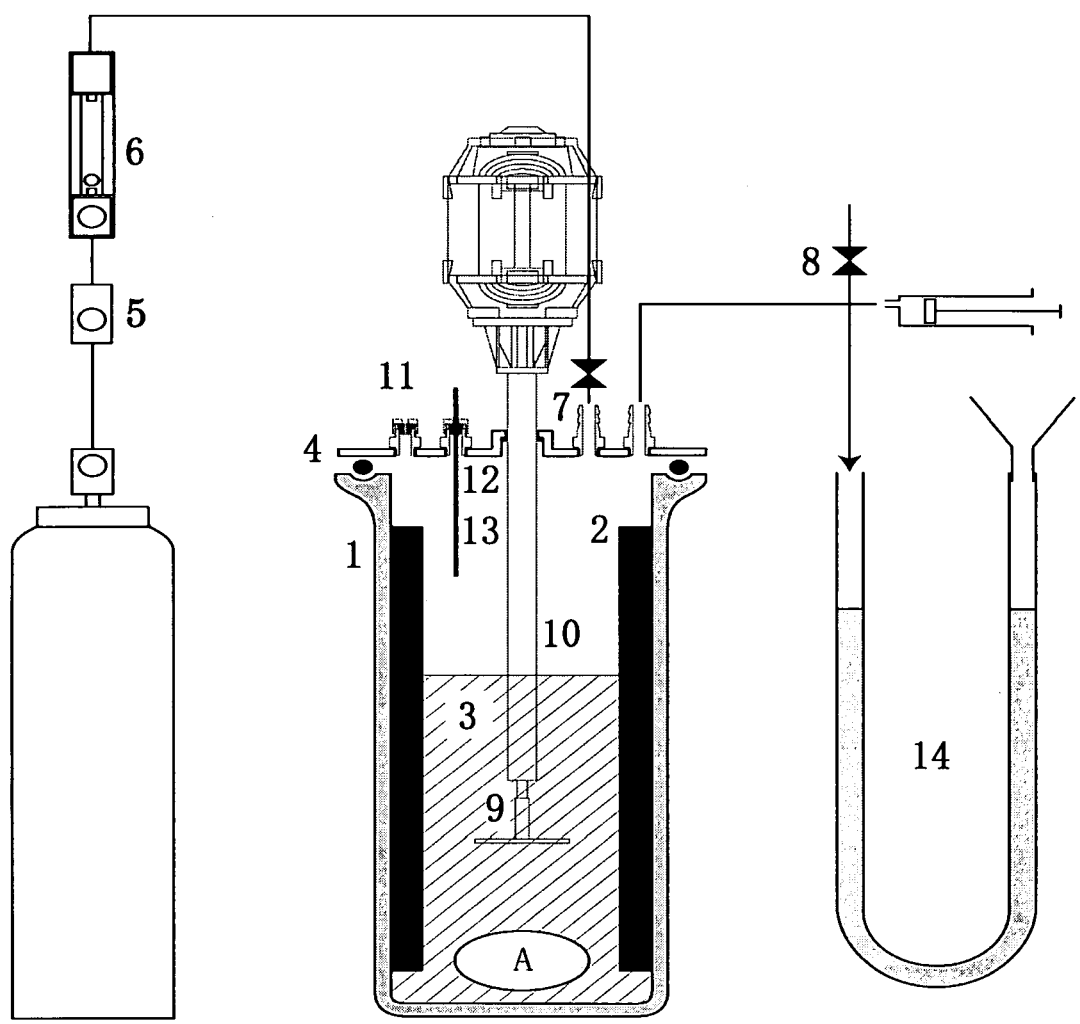
FIG. 5 is a schematic explanatory diagram of an example of the separation apparatus according to the present embodiment.

FIG. 5 shows an example of the separation apparatus. An aqueous solution 3 mixed with a fixed quantity of sulfuric acid, an antifoaming material, and salts is placed in a container 1 (preferably one having a baffle plate 2) that can be made airtight.

After the container 1 is airtightly sealed using a top cover 4, a fixed quantity of nitrogen gas is injected into the container 1 through an injection port 7 connected via a pressure regulator 5 and a flow meter 6, and is then exhausted through an exhaust port 8. A timer-controlled homogenizer 9 is started, and the aqueous solution 3 and the gas phase unit 10 inside the container 1 are subjected to nitrogen substitution for a fixed period of time.

After the nitrogen substitution step is completed, the top cover 4 is removed, and the sample A is placed in the container 1. The top cover 4 is once again sealed onto the container 1, and the gas phase unit 10 inside the container 1 is then subjected to nitrogen substitution for a fixed period of time. After the nitrogen substitution of the gas phase has been completed, the timer-controlled homogenizer 9 is operated for a fixed period of time to homogenize the sample A and obtain separated gases in the gas phase unit 10.

The separated gas collected in the gas phase unit 10 is extracted from an extraction port 11 by using a gastight syringe, and is injected into a gas chromatograph to quantitatively analyze the gas components.

When the separated gas is extracted from the extraction port 11, the detected concentration of the separated gas obtained in the gas phase 10 may be corrected using e.g., a temperature sensor 12, pressure sensor 13, or volume regulator 14.

[Analysis Method 2]

Figure 6:
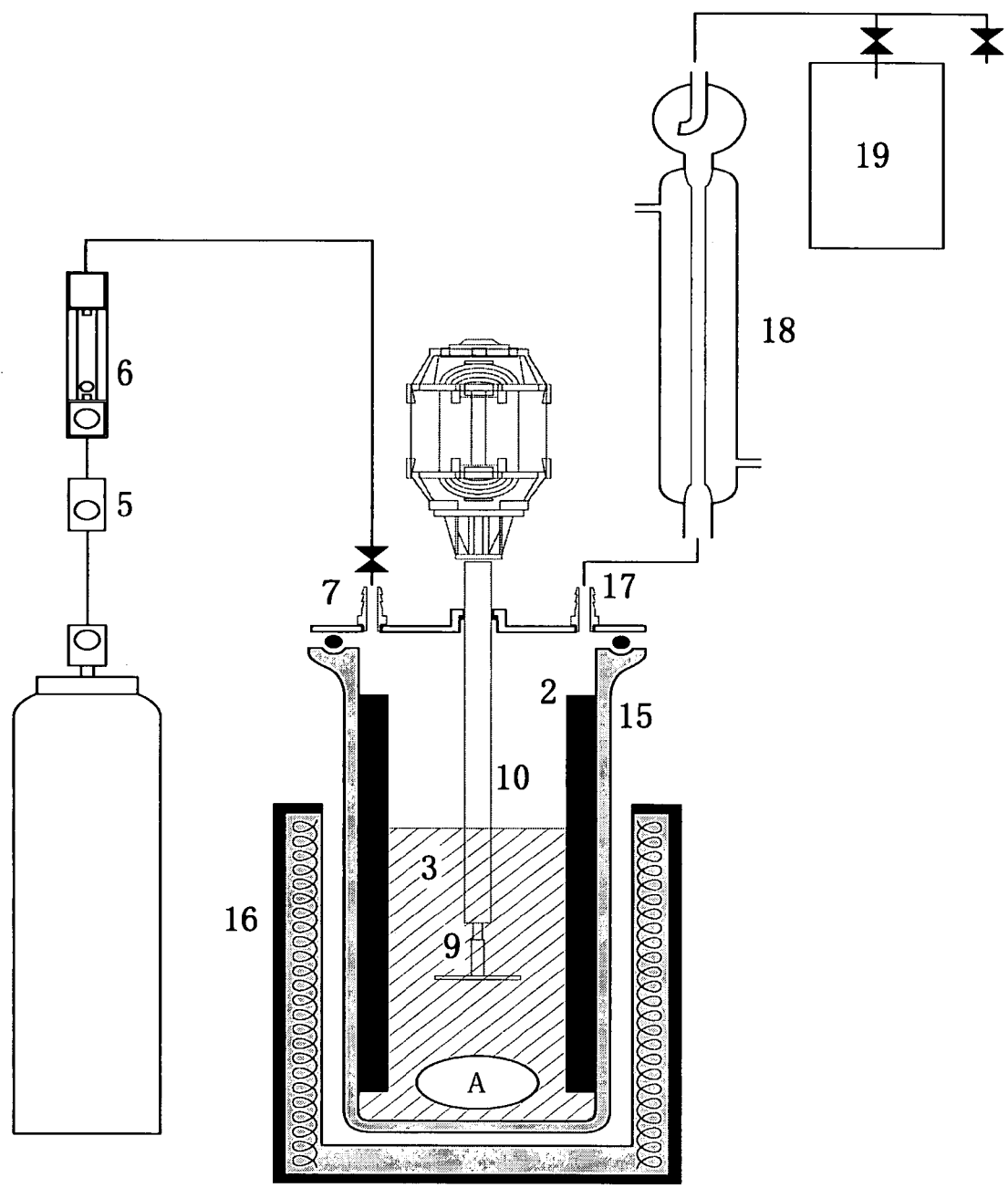
FIG. 6 is a schematic explanatory diagram of an example of the separation apparatus according to the present embodiment.

A separation apparatus such as that shown in FIG. 6 may be used when a sample that still contains highly soluble gas components is analyzed or quantified using gas sensors or detection tubes.

Specifically, the container 1 is heated using a heater 16 while nitrogen gas is fed to the container 15, and the sample A is simultaneously homogenized in the same manner as in analysis method 1. Separated gas is obtained from a discharge port 17 in a Tedlar bag 19 by way of a cooling unit 18, and the separated gas is quantitatively analyzed using gas sensors or detection tubes.

[Analysis Method 3]

Figure 7:
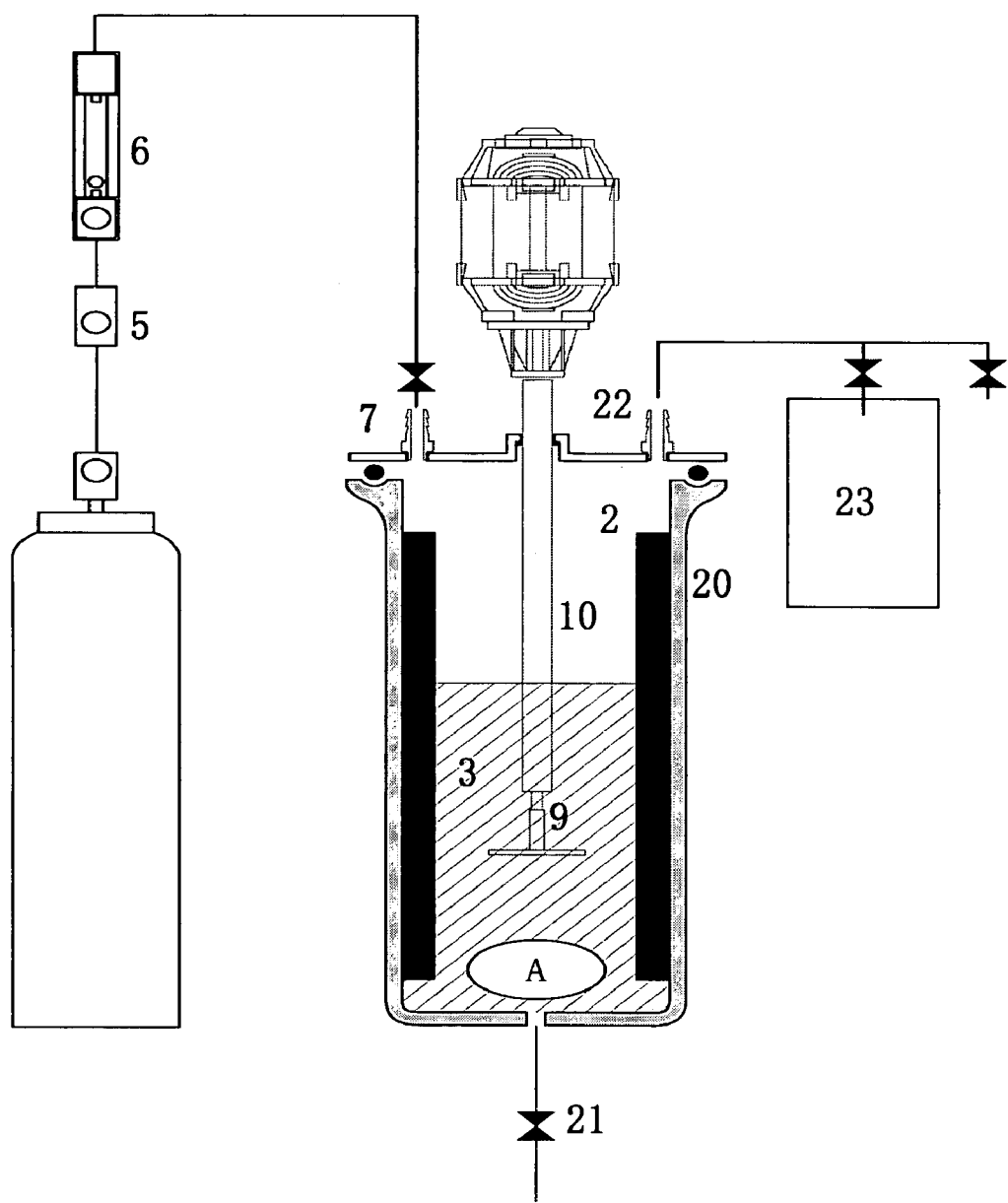
FIG. 7 is a schematic explanatory diagram of an example of the separation apparatus according to the present embodiment.

A separation apparatus such as that shown in FIG. 7 may be used as another example of analysis method 2.

Specifically, after the sample A has been homogenized in the same manner as in analysis method 1 described above, salt-saturated aqueous solution is injected into a container 20 through an injection port 21 disposed in the upper portion or lower portion of the container 20. Separated gas is obtained from a discharge port 22 in a Tedlar bag 23, and the separated gas is quantitatively analyzed using gas sensors or detection tubes.

In view of the foregoing, the present invention allows a specimen having a prescribed weight to be homogenized inside an airtight container, whereby the carbon monoxide, lower hydrocarbon groups, and other gas components contained in the specimen are kept inside the airtight container and do not dissipate when transferred to the gas phase.

Specifically, a specimen having a minimized surface area is placed in an airtight container without being homogenized, shredded, or otherwise pretreated, and is thereafter homogenized inside the airtight container, whereby the dissipation of the gas components to the exterior of the airtight container can be minimized, and errors due to the dissipation of gas components from the specimen prior to placement in the airtight container can be reduced.

The gas components contained in the specimen can therefore be more accurately analyzed, and the carbon monoxide and lower hydrocarbon groups can be quantitatively analyzed to allow fish and meat as the specimen to be more accurately identified as having been subjected to CO-treatment or smoking treatment, or as having not been so treated.

The gas components can, for example, be prevented from remaining in the liquid phase during homogenization by, e.g., saturating salts in the solution inside the airtight container in order to facilitate the movement of gas components from the liquid phase to the gas phase, or by otherwise reducing the solubility of the gases.

In other words, by reducing the solubility of the gases, an environment can be formed that facilitates the movement of the gas components to the gas phase, and errors due to gas components remaining in the liquid phase can be reduced.

Also, the pH of the aqueous solution inside the airtight container is set to 2.77 or less, whereby the gas components in Hb and Mb are more easily dissociated, the movement of the gas components physically dissolved in meat to the gas phase is facilitated, and errors due to the failure of the gas components in the Hb and Mb to dissociate can be reduced.

Therefore, the present invention solves the problems of the KH method, is able to detect gas components contained in a specimen with higher accuracy and good reproducibility, and can quantitatively analyze gas components, e.g., carbon monoxide and lower hydrocarbon groups contained in fish and meats to more reliably identify whether fish and meats have been CO treated, are smoked products, or are untreated products.

What is claimed is:

1. A method for quantitatively analyzing gas components contained in a specimen, the method comprising:
    placing a saturated aqueous solution in an airtight container;
    placing an untreated specimen having an unchanged solid state and a prescribed weight in the airtight container in which the saturated aqueous solution is placed;
    homogenizing the specimen in the airtight container to separate the gas components from the specimen; and
    quantitatively analyzing the gas components separated from the homogenized specimen;
    wherein the specimen is homogenized in a state in which an interior of the airtight container is heated or decompressed;
    wherein the quantitative analysis of the gas components separated from the homogenized specimen is performed to identify fish or meat as the specimen as being carbon monoxide treated, smoked, or untreated;
    wherein the aqueous solution has a pH of 2.77 or less.

2. The method for analyzing gas components according to claim 1, wherein the gas components separated from the homogenized specimen comprise carbon monoxide and lower hydrocarbon groups.

3. The method for analyzing gas components according to claims 1 or 2, wherein the gas components separated from the homogenized specimen inside the airtight container temperature or pressure corrected.

4. The method for analyzing gas components according to claims 1 or 2, wherein additional saturated aqueous solution is injected into the airtight container to extract the gas components separated from the homogenized specimen inside the airtight container.

5. The method for analyzing gas components according to claim 3, wherein additional saturated aqueous solution is injected into the airtight container to extract the gas components separated from the homogenized specimen inside the airtight container.

6. The method for analyzing gas components according to claim 5, wherein the gas components separated from the homogenized specimen inside the airtight container are quantified using gas chromatography and gas sensors or detection tubes.

7. The method for analyzing gas components according to any of claims 1 or 2, the method comprising:
    providing an airtight container capable of accommodating the specimen; and
    providing a homogenizer capable of homogenizing the specimen in the airtight container while maintaining an airtight state.

8. The method for analyzing gas components according to claim 3, the method comprising:
    providing an airtight container capable of accommodating the specimen; and
    providing a homogenizer capable of homogenizing the specimen in the airtight container while maintaining an airtight state.

9. The method for analyzing gas components according to claim 4, the method comprising:
    providing an airtight container capable of accommodating the specimen; and providing a homogenizer capable of homogenizing the specimen in the airtight container while maintaining an airtight state.

10. The method for analyzing gas components according to claim 5, the method comprising:
    providing an airtight container capable of accommodating the specimen; and
    providing a homogenizer capable of homogenizing the specimen in the airtight container while maintaining an airtight state.

11. The method for analyzing gas components according to claim 6, the method comprising:
    providing an airtight container capable of accommodating the specimen; and
    providing a homogenizer capable of homogenizing the specimen in the airtight container while maintaining an airtight state.

12. A method for quantitatively analyzing gas components comprising carbon monoxide and lower hydrocarbon groups contained in fish, meat, or another specimen, and identifying the specimen to be CO treated, smoked, or untreated, the method comprising:
    placing a saturated aqueous solution having a pH of 2.77 or less in an airtight container;
    mixing a liquid phase and gas phase in the airtight container and simultaneously substituting an inert gas in place of the gas phase, and thereafter placing an untreated specimen having an unchanged solid state and a prescribed weight in the airtight container;
    releasing the gas components into the inert gas by homogenizing the specimen, the liquid phase, and the inert gas in the airtight container; and
    quantitatively analyzing the carbon monoxide and lower hydrocarbon groups released into the inert gas.

13. A method for quantitatively analyzing gas components comprising carbon monoxide and lower hydrocarbon groups contained in fish, meat, or another specimen, and identifying the specimen to be CO treated, smoked, or untreated, the method comprising:
    placing an aqueous solution having a pH of 2.77 or less in an airtight container;
    mixing a liquid phase and gas phase in the airtight container and simultaneously substituting an inert gas in place of the gas phase, and thereafter placing an untreated specimen having an unchanged solid state and a prescribed weight in the airtight container;
    releasing the gas components into the inert gas by homogenizing the specimen, the liquid phase, and the inert gas in the airtight container in a state in which the airtight container has been heated or decompressed; and
    quantitatively analyzing the carbon monoxide and lower hydrocarbon groups released into the inert gas.

* * * * *